United States Patent
Civelek et al.

(10) Patent No.: US 11,732,147 B2
(45) Date of Patent: Aug. 22, 2023

(54) MATERIAL FOR 3D PRINTING AND METHOD OF MAKING AND USE OF THE MATERIAL

(71) Applicants: Emre Civelek, Bergkamen (DE); Thomas Veit, Muenster (DE)

(72) Inventors: Emre Civelek, Bergkamen (DE); Thomas Veit, Muenster (DE)

(73) Assignee: DREVE PRODIMED GMBH, Unna (DE)

( * ) Notice: Subject to any disclaimer, the term of this patent is extended or adjusted under 35 U.S.C. 154(b) by 904 days.

(21) Appl. No.: 16/551,967

(22) Filed: Aug. 27, 2019

(65) Prior Publication Data
US 2020/0115571 A1 Apr. 16, 2020

(30) Foreign Application Priority Data
Oct. 11, 2018 (DE) .......................... 102018125177.7

(51) Int. Cl.
| | |
|---|---|
| *C08F 290/06* | (2006.01) |
| *B33Y 70/00* | (2020.01) |
| *C09D 11/101* | (2014.01) |
| *B33Y 10/00* | (2015.01) |
| *B29C 64/124* | (2017.01) |
| *C09D 11/107* | (2014.01) |
| *B33Y 80/00* | (2015.01) |
| *A61C 7/08* | (2006.01) |
| *B29K 83/00* | (2006.01) |
| *B29L 31/00* | (2006.01) |

(52) U.S. Cl.
CPC .......... *C09D 11/101* (2013.01); *B29C 64/124* (2017.08); *B33Y 10/00* (2014.12); *B33Y 70/00* (2014.12); *C09D 11/107* (2013.01); *A61C 7/08* (2013.01); *B29K 2083/00* (2013.01); *B29K 2995/0026* (2013.01); *B29K 2995/0046* (2013.01); *B29L 2031/753* (2013.01); *B33Y 80/00* (2014.12); *C08F 290/068* (2013.01)

(58) Field of Classification Search
CPC ... A61C 7/08; A61F 5/56; A61L 27/18; B29C 64/124; B29C 64/135; B29K 2083/00; B29K 2995/0026; B29K 2995/0046; B33Y 10/00; B33Y 70/00; B33Y 70/10; C08F 2/50; C08F 283/124; C08F 290/068; C08F 297/026; C08G 77/442; C08K 3/36; C09F 11/101; C09F 11/107; C08L 83/04
USPC ..................... 522/92, 99, 148, 172
See application file for complete search history.

(56) References Cited

U.S. PATENT DOCUMENTS

| | | |
|---|---|---|
| 5,236,637 A | 8/1993 | Hull |
| 7,438,846 B2 | 10/2008 | John |
| 7,982,474 B1 | 7/2011 | Hefner |
| 9,120,270 B2 | 9/2015 | Chen |
| 2013/0292862 A1 | 11/2013 | Joyce |
| 2017/0275406 A1 | 9/2017 | Matsumoto |
| 2019/0123917 A1 | 1/2019 | Drazba |
| 2019/0112430 A1 | 4/2019 | Yook |

FOREIGN PATENT DOCUMENTS

| | | | | |
|---|---|---|---|---|
| CN | 104914675 A | * | 9/2015 | |
| EP | 2676633 A1 | * | 12/2013 | |
| WO | WO-2017112751 A1 | * | 6/2017 | ........... B29C 64/124 |

* cited by examiner

*Primary Examiner* — Sanza L. McClendon
(74) *Attorney, Agent, or Firm* — Andrew Wilford

(57) ABSTRACT

A transparent, elastic, and biocompatible 1K silicone for additive manufacturing that can be printed by stereolithographic processes, includes at least
- 25-75% by weight of a monomeric or oligomeric dimethacrylate based on silicone or silicone urethanes having a viscosity of <100 Pa·s,
- 20-50% by weight of one or more monomeric/oligomeric cyclic (meth)acrylates having a viscosity of <0.5 Pa·s,
- 1-25% by weight of silicone oil having a viscosity of <1 Pa·s,
- 0.5-20% by weight of fillers with a particle size of <100 μm,
- 0.1-5% by weight of one or a combination of a plurality of photoinitiators whose absorption is in the wavelength range of the laser beam or irradiation source used.

9 Claims, No Drawings

MATERIAL FOR 3D PRINTING AND METHOD OF MAKING AND USE OF THE MATERIAL

FIELD OF THE INVENTION

The invention relates to an elastomeric material for 3D printing and to a method of making and using this material.

BACKGROUND OF THE INVENTION

"Additive manufacturing" is to be understood to also include so-called "stereolithographic manufacturing."

In the case of conventional elastic materials for 3D printing, in which construction is performed layer by layer, silicone-like elastic materials are known that contain little or no amount of siloxane groups, have no biocompatibility, are not transparent, and/or cannot be printed using the known DLP (Digital Light Processing) method. During the DLP method, layers are formed through solidification of the liquid component due to irradiation with a light source, particularly with a wavelength between 355 nm and 410 nm. Two 3D printing techniques are known. The first technique was described by Hull in 1984 with U.S. Pat. No. 5,236,637. Other known examples are described in U.S. Pat. Nos. 7,438,846, 7,982,474 by M. Joyce, US published patent application 2013/0292862 by Y. Pan et al., US published patent application 2013/0295212 by Y. Pan et al., and numerous other references. Materials for processing using the DLP method are typically limited, and there is a need for new resins that provide different material properties for different product groups in order to fully exploit the potential of three-dimensional manufacturing.

OBJECT OF THE INVENTION

It is therefore the object of the present invention to provide an improved 3D printing material that overcomes the disadvantages of the above-described materials.

SUMMARY OF THE INVENTION

This object is attained according to the invention by a radiation-curing, low-viscosity, transparent, and biocompatible 1K silicone resin material that is used to make elastic three-dimensional medical products and molded parts for medical technology. Particularly focus is in the field of otology earpieces (otoplastics) and dental applications such as gingival masks and mouth guards as well as orthodontic applications such as positioners and appliances (for example snoring appliances, aligner appliances). The applications mentioned are to be regarded as examples and not as exclusive. It preferably consists of at least 50% siloxane groups, a siloxane copolymer, or at least one component that comprises the group of siloxanes. Included are: a) 25-75% by weight of a monomeric or oligomeric dimethacrylate based on siloxanes or siloxane-urethanes having a viscosity of <100 Pa·s; b) 20-50% by weight of one or more monomeric/oligomeric cyclic (meth)acrylates having a viscosity of <0.5 Pa·s; up to 20% by weight of an aliphatic or cycloaliphatic dimethacrylate having a viscosity of <10 Pa·s; c) 1-25% by weight of silicone oil having a viscosity of <1 Pa·s; d) 0.5-20% by weight of fillers with a particle size of <100 µm; e) 0.1-5% by weight of one or of a combination of a plurality of photoinitiators whose absorption lies in the wavelength range of the laser beam used or the irradiation source used; up to 0.5% by weight of one or more anaerobic inhibitors; up to 5% by weight of colorants; up to 5% by weight of conventional additives such as UV stabilizers, adhesion promoters, and flow additives, the proportion of all components together constituting 100% by weight.

The specifications of the individual components and the different variants of the photoinitiators and additives that are indicated in % by weight are described in detail below. What is novel and inventive about this composition is, in particular, that it contains at least 50% of siloxane groups that are terminally functionalized with (meth)acrylate and, at the same time, have the properties of transparency, elasticity, and biocompatibility, and can be combined in a 1K material and manufactured additively. As stated in the prior art, while similar materials do exist, none of these materials unites the enumerated properties in one material. The advantage of the terminally functionalized siloxane (meth)acrylates over other groups that are terminally functionalized with (meth)acrylate is that they are physiologically compatible, which is why they are frequently used in the medical device industry. Other terminal (meth)acrylates can be: aliphatic or cycloaliphatic urethane (meth)acrylates, aliphatic or cycloaliphatic (meth)acrylates, and n-ethoxylated bisphenol A di(meth)acrylates.

In particular, the invention relates to a transparent, elastic, and biocompatible 1K silicone that can be printed by additive processes for the purpose of additive manufacturing.

The invention relates to materials that are produced by the "Digital Light Processing" (DLP) stereolithographic process for the manufacture of solid, transparent, elastic, biocompatible, and three-dimensional earpieces (otoplastics, gingival masks, and mouth guards, as well as orthodontic applications such as positioners and appliances (for example snoring appliances, aligner appliances) and obtained from low-viscosity 1K materials with a siloxane content of at least 50%.

It is important to mention that the material is used to make elastic, transparent, biocompatible, and three-dimensional earpieces (earpieces), gingival masks, and mouth guards, as well as orthodontic applications such as positioners and appliances (for example snoring appliances, aligner appliances) with a minimum of 50% siloxane groups is inventive and novel.

In general, a transparent, elastic and biocompatible 1K material is used in the context of the present invention to make a three-dimensional earpiece (otoplastic), gingival mask, or mouth guard and for orthodontic applications such as positioners and appliances (for example snoring appliances, aligner appliances) with a minimum proportion of siloxane groups of 50% and is to be described by the following properties:

The invention provides a siloxane composition that cures in a few seconds under (UV) light and can be used for the manufacture of transparent, elastic, biocompatible, and three-dimensional earpieces (otoplastics), gingival masks, or a mouth guard, as well as for orthodontic applications such as positioners and appliances (for example snoring appliances, aligner appliances). In particular, the compositions provided are prepared from siloxane-containing (meth)acrylates, with alipathic or cycloaliphatic di(meth)acrylates, silicone oils, and fillers also being used in addition to cyclic (meth)acrylates. Through the use of one or more of the combination of a plurality of photoinitiators, the existing (meth)acrylates enable rapid and precise curing of the composition.

BRIEF DESCRIPTION OF THE RELATED MATERIALS

Fast-curing compositions that have a high siloxane content and elastic properties, are transparent and biocompatible, and can be produced by additive processes have been nonexistent until now. These properties can be occasionally found in some products, but not completely in this combination. These products will therefore be compared with the invention below. The manufacture of silicone elastomers by a additive process for the production of molded parts was described by Wacker Chemie AG in patent app. WO2016071241. This application did not describe any new materials, but rather a new method for the preparation of silicones. Since this method is a 2K material and drops are placed within the process that are subsequently radiation-cured, this silicone cannot be compared to the present invention. On the one hand, the digital light-processing method enables accuracies of from 20 µm to 100 µm (standard: 100 µm) per layer thickness to be achieved, which are essential for biomedical products such as earpieces or gingival masks or mouth guards as well as orthodontic applications such as positioners and appliances (for example snoring appliances, aligner appliances). On the other hand, the 2K silicone from Wacker AG hardens after mixing without irradiation, which is not the case with a one-component material. The reason for this lies in the chemical mechanism of the reactions. While the polymerization of the 2K silicone from Wacker AG is activated with a catalyst after the mixing of the two components and accelerated by (UV) light, the photon initiator or combination of photon initiators used in the present invention requires or require (UV) light in order for the polymerization to be activated. This ensures a longer pot life. The "blocked dual-curing silicone resins for additive manufacturing" described by Carbon Inc. with WO 2017112751, which does not contain a high % by weight of siloxane groups, cannot be printed by standardized stereolithography such as the DLP method and is not transparent. In addition, Carbon Inc. describes a two-component resin that is first cured by (UV) light and then treated with heat in order to have the final properties described in the aforementioned patent application. The material described in this invention does not require subsequent processing with heat in order to have mechanically strong properties.

UV-curable siloxanes are described inter alia by Shin Etsu Chemical Co. in EP 3222689. The mechanical properties and load capacities of the silicones produced are far below the standard for producing stable moldings by stereolithography, particularly by the DLP method. Photocuring silicones are also described by the Dow Corning Corporation in patent application WO 2017155919. These silicones are also not suitable for manufacturing by stereolithographic processes, particularly the DLP method.

The entire process, beginning with three-dimensional printing, in which layer is built upon layer, and through to the post-cleaning and post-curing of the built objects, is analogous to that used for the known resins in 3D printing as explained in the article "Digitale Fertigung in der Dentaltechnologie mittels additiver Fertigungsverfahren" ["Digital manufacturing in dental technology using additive manufacturing processes"] by C. Glodecki, A. Neumeister, Jahrbuch Digitale Dental Technologies 2017, pp. 97-105. This transferability and compatibility was able to be adapted and optimized by the inventors by selecting the correct components and changing the proportions within the composition explicitly for the DLP method. Flowability in particular is crucial for the construction process, post-cleaning, and the properties obtained as well as the mechanical strength. Add to this the properties of transparency, biocompatibility, and ease of use, which were not neglected.

To explain the ease of transferability of the new material to the DLP method, mention should be made of the (meth) acrylate functionalities, which are radically polymerized and also present in the resins that are commercially available for the DLP method. The abovementioned patent by Wacker Chemie AG reports pure two-component silicones that utilize a catalyst system that is accelerated by UV light in order to subsequently perform the addition-crosslinking reaction according to the known mechanism of hydrosilylation. Due to their high reactivity transfer to the entire system (including non-irradiated regions), these materials are sensitive to the DLP method, since the inputting of energy enables the entire vessel (the container for the liquid resin) can be cured homogeneously without the need to be irradiated in its entirety. This important aspect was taken into account in the invention presented here and changed in such a way that this problem could be disregarded.

Although elastic compositions with a low proportion of siloxane groups have been developed with the product of carbon, it must be pointed out that this is a 2K material that must undergo heat treatment after the printing process in order to obtain the described properties and a finished product.

Furthermore, there is a need for transparent, biocompatible 1K materials in DLP printing that have properties similar to those of classic silicone—i.e., elastic, physiologically harmless and mechanically strong properties. Known transparent elastic 3D printing materials can either not be printed by the standard DLP method or are not biocompatible, have no transparency, and/or cannot be classified within the range of the classic silicones on account of their composition.

Therefore, a need exists in the art for transparent, elastic and biocompatible 3D printable materials having a high proportion of siloxane groups that can be printed by the standard DLP method.

Various materials exist in the prior art that have the individual properties, but there is no material that combines all of these properties at the same time.

With the present invention, this has been achieved. The invention has thus made a material available that unites all of these properties.

The formulation according to the invention contains both acrylate- and methacrylate-functionalized groups and can be polymerized exclusively by a corresponding photoinitiator or a combination of a plurality of photoinitiators in the UV light range and thus cured. In particular, the wavelength ranges from 350 to 410 nm are suitable for this purpose. The siloxane-containing (meth)acrylates can also contain other functionalities such as a urethane group, for example. Among other things, this group provides intramolecular interactions for mechanically strong properties.

In particular, the invention provides a composition comprising the following structures:

a) a polymer having the structural formula:

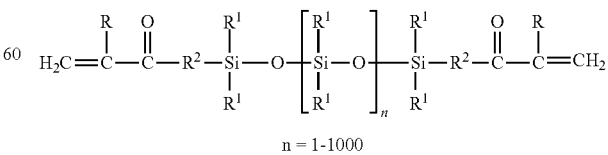

n = 1-1000 where R is a hydrogen or a $C_{1-20}$ alkyl that can be substituted or unsubstituted or is an unsaturated radical curing group. $R^1$ is also a $C_{1-20}$ alkyl that can be substituted or unsubstituted. $R^2$ describes a $C_{1-20}$ alkyl and/or a urethane group that is to be presented subsequently:

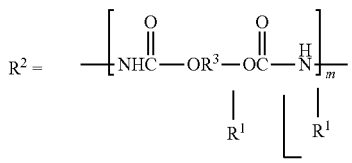

$R^3$ represents a C1-6 alkyl that can be substituted or unsubstituted or cyclically saturated or unsaturated.

b) one or more monomers having the structural formula:

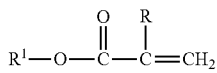

where R is a hydrogen or a $C_{1-20}$ alkyl that can be substituted or unsubstituted or is an unsaturated radical curing group. $R^1$ is a $C_{1-20}$ alkyl that can be substituted or unsubstituted or cyclically saturated or unsaturated, or that can consist of two coupled cycles or mutually independent cycles.

According to the invention, an aliphatic or cycloaliphatic dimethacrylate having a viscosity of <10 Pa·s.

c) a silicone oil having the structural formula:

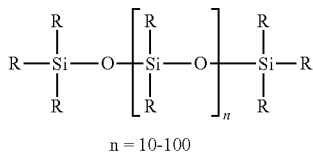

n = 10-100 where R represents a $C_{1-20}$ alkyl that can be substituted or unsubstituted and cyclically saturated or unsaturated.

d) a pyrogenic or precipitated silicic acid that can be hydrophilically or hydrophobically modified.

e) one or a combination of photoinitiator(s) having the structural formula:

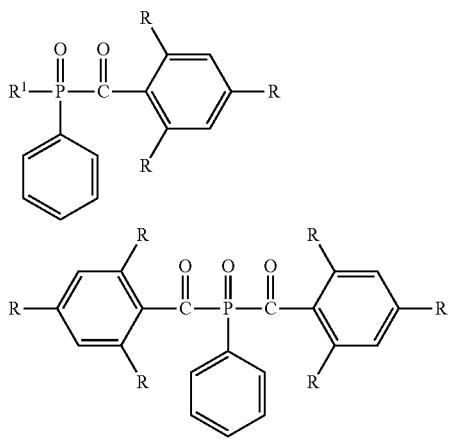

where R is hydrogen or a $C_{1-6}$ alkyl that can be substituted or unsubstituted or cyclically saturated and unsaturated. $R^1$ is an alkoxy group or $C_{1-6}$ alkyl that can be substituted or unsubstituted.

The solution of the present invention consists in providing a low-viscosity, transparent, and biocompatible silicone resin formulation for the production of medical devices by conventional stereolithography that satisfies the both the mechanical—particularly a tensile elongation of >100%—and toxicological requirements, as well as those placed on the abovementioned processes. In this case, it was found that a low-viscosity silicone oil with a viscosity of <1 Pa·s and composed of one or more oligomeric di(meth)acrylates based on silicone urethanes and that also has a cyclic (meth)acrylate with a viscosity of <0.5 Pa·s can be used for the technique of stereolithography and, upon being cured by laser or under (UV) light of the appropriate wavelength, yields pre-cured molded bodies that are characterized by a green strength and are far softer and more flexible than the end products. Surprisingly, it was found that, by switching the formulation, not only elastic, but also initially soft, flexible, plastic-like bodies with a silicone content of 50% and outstanding mechanics that solidify after reworking can be produced. In addition, it was possible to prepare compositions that have already formed rigid structures as green bodies and also do not exhibit soft properties later on.

Accordingly, it is the object of the present invention to provide a low-viscosity, radiation-curable, biocompatible resin formulation that can be initially yellow but also transparent and, after use in stereolithography, more specifically the DLP method and subsequent reworking, yields transparent elastic molded bodies having the following composition:

a) 25-75% by weight of a monomeric or oligomeric dimethacrylate based on silicone or silicone urethanes having a viscosity of <100 Pa·s;

b) 20-50% by weight of one or more monomeric/oligomeric cyclic (meth)acrylates having a viscosity of <0.5 Pa·s, according to the invention, up to 20% by weight of an aliphatic or cycloaliphatic dimethacrylate having a viscosity of <10 Pa·s;

c) 1-25% by weight of silicone oil having a viscosity of <1 Pa·s;

d) 0.5-20% by weight of fillers with a particle size of <100 µm;

e) 0.1-5% by weight of one or a combination of a plurality of photoinitiators whose absorption is in the wavelength range of the laser beam or irradiation source used, up to 0.5% by weight of one or more anaerobic inhibitors, up to 5% by weight of colorants, up to 5% by weight of conventional additives such as UV stabilizers, adhesion promoters, and flow additives, the proportion of all of the components together being 100% by weight.

Preferably, a mixture according to the invention contains:

a) 30-65% by weight of a monomeric or oligomeric dimethacrylate based on silicone urethanes having a viscosity of <100 Pa·s;

b) 10-25% by weight of one or more monomeric/oligomeric cyclic (meth)acrylates having a viscosity of <0.5 Pa·s, up to 20% by weight of an aliphatic or cycloaliphatic dimethacrylate having a viscosity of <10 Pa·s;

c) 1-25% by weight of silicone oil having a viscosity of <1 Pa·s;

d) 3-10% by weight of fillers with a particle size of <100 µm;

e) 0.2-2% by weight of one or a combination of a plurality of photoinitiators whose absorption is in the wavelength range of the laser beam or irradiation source used, up to 0.5% by weight of one or more anaerobic inhibitors, up to 5% by weight of colorants, up to 5% by weight of conventional additives such as UV stabilizers, adhesion promoters, and flow additives, the proportion of all of the components together being 100% by weight.

Examples of suitable compounds of component (a) include functional oligomers of a combination of silicone urethane acrylate oligomers, silicone acrylate oligomers, silicone urethane methacrylate oligomers, or silicone methacrylate oligomers. Preferably, monomeric or oligomeric di(meth)acrylates based on siloxanes and urethanes are used, particularly a combination of silicone urethane acrylate oligomers. Combinations with an increased proportion by weight of silicone within the combination of silicone urethane acrylate oligomers are preferred.

The monomers or oligomers of cyclic (meth)acrylates having a viscosity of <0.1 Pa·s used as component (b) in the formulation according to the invention are commercially available from Arkema. Known representatives of these molecules are isobornyl acrylate and derivatives thereof, trimethylcyclohexyl (meth) acrylates and derivatives thereof, tert. butylcyclohexyl (meth)acrylate and associated derivatives, cyclic trimethylpropane formal (meth)acrylate and derivatives thereof, and isobornylcyclohexyl (meth) acrylate and derivatives thereof. Preferably, the latter are used with a viscosity <0.02 Pa·s.

The following can be used as a compound for example: Urethane (meth)acrylates having a functionality of <4, which are known in the art and can be prepared in a known manner, for example by converting a hydroxyl-terminated polyurethane with methacrylic acid to the corresponding urethane methacrylate, or by reacting an isocyanate-terminated prepolymer with hydroxy methacrylates. Such methods are known from EP 0579503, for example. Urethane (meth acrylates are also commercially available and sold, for example, under the name PC-Cure® by Piccadilly Chemicals, under the product name CN 1963 by Sartomer, under the name Photomer by Cognis, under the name Ebecryl by UCB, and under the name Genomer® by Rahn. Urethane (meth)acrylates that are preferably used are those that are n<4 functionalized, have viscosities of <15 Pa·s, have a molecular weight of <2000, and have been prepared from aliphatic starting materials. In particular, the isomer mixture obtained from HEMA and TMDI, 7,7,9- (or 7,9,9-) trimethyl-4,13-di-oxo-3,14-dioxa-5,12-diazahexadecane-1,16-diol-dimethacrylate, is used.

The components (c) mentioned in the invention can be linear non-reactive silicone oils having a siloxane unit of from 10 to 100 and a viscosity of from <0.01 to 0.1 Pa·s. Such products can be purchased from Momentive (Leverkusen) or Wacker Chemie AG.

Example 1

| | |
|---|---|
| 50.6*(1 − x/100) wt % | silicone urethane acrylate (viscosity < 20 Pa · s) |
| 36.1*(1 − x/100) wt % | trimethylcyclohexyl acrylate (viscosity < 0.01 Pa · s) |
| 9.2*(1 − x/100) wt % | silicone oil (viscosity < 0.015 Pa · s) |
| 3.1*(1 − x/100) wt % | pyrogenic silicic acid |
| 1.0*(1 − x/100) wt % | phenylbis(2,4,6-trimethylbenzoyl)phosphine oxide |
| Color: | clear, transparent |
| Stretch to break (%): | 250 ± 8 |
| Tensile strength (MPa): | 4.5 ± 0.1 |
| Durometer: | 70 Shore A |

Example 2

| | |
|---|---|
| 56.3*(1 − x/100) wt % | silicone urethane acrylate (viscosity < 20 Pa · s) |
| 28.2*(1 − x/100) wt % | isobornyl acrylate (viscosity < 0.015 Pa · s) |
| 11.2*(1 − x/100) wt % | silicone oil (viscosity < 0.015 Pa · s) |
| 3.3*(1 − x/100) wt % | pyrogenic silicic acid |
| 1.0*(1 − x/100) wt % | phenylbis(2,4,6-trimethylbenzoyl)phosphine oxide |
| Color: | clear, transparent |
| Stretch to break (%): | 201 ± 6 |
| Tensile strength (MPa): | 3.8 ± 0.1 |
| Durometer: | 60 Shore A |

Example 3

| | |
|---|---|
| 52.1*(1 − x/100) wt % | silicone urethane acrylate (viscosity < 20 Pa · s) |
| 32.8*(1 − x/100) wt % | isobornyl acrylate (viscosity < 0.015 Pa · s) |
| 11.0*(1 − x/100) wt % | silicone oil (viscosity < 0.015 Pa · s) |
| 1.1*(1 − x/100) wt % | pyrogenic silicic acid |
| 1.0*(1 − x/100) wt % | phenylbis(2,4,6-trimethylbenzoyl)phosphine oxide |
| Color: | clear, transparent |
| Stretch to break (%): | 100 ± 5 |
| Tensile strength (MPa): | 3.4 ± 0.2 |
| Durometer: | 50 Shore A |

Example 4

| | |
|---|---|
| 54.9*(1 − x/100) wt % | silicone urethane acrylate (viscosity < 20 Pa · s) |
| 30.0*(1 − x/100) wt % | modified isobornyl acrylate (viscosity < 0.015 Pa · s) |
| 8.8*(1 − x/100) wt % | cyclic trimethylpropane formal (meth)acrylate (viscosity < 0.015 Pa · s) |
| 4.0*(1 − x/100) wt % | silicone oil (viscosity < 0.015 Pa · s) |
| 1.1*(1 − x/100) wt % | pyrogenic silicic acid |
| 1.2*(1 − x/100) wt % | phenylbis(2,4,6-trimethylbenzoyl)phosphine oxide |
| Color: | clear, transparent |
| Stretch to break (%): | 90 ± 5 |
| Tensile strength (MPa): | 3.9 ± 0.2 |
| Durometer: | 60 Shore A |

Example 5

| | |
|---|---|
| 53.4*(1 − x/100) wt % | silicone urethane acrylate (viscosity < 20 Pa · s) |
| 32.5*(1 − x/100) wt % | modified isobornyl acrylate (viscosity < 0.015 Pa · s) |
| 3.3*(1 − x/100) wt % | cyclic trimethylpropane formal meth)acrylate (viscosity < 0.015 Pa · s) |
| 3.5*(1 − x/100) wt % | 2-ethyl hexyl acrylate (viscosity < 0.015 Pa · s) |
| 4.1*(1 − x/100) wt % | silicone oil (viscosity < 0.015 Pa · s) |
| 2.0* (1 − x/100) wt % | pyrogenic silicic acid |

-continued

| | |
|---|---|
| 1.2*(1 − x/100) wt % | phenylbis(2,4,6-trimethylbenzoyl)phosphine oxide |
| Color: | clear, transparent |
| Stretch to break (%): | 105 ± 5 |
| Tensile strength (MPa): | 3.1 ± 0.2 |
| Durometer: | 45 Shore A |

Comparison of 3D-Printable Silicone

| Characteristics | Carbon Silicone | Wacker AG | Keyence | Invention |
|---|---|---|---|---|
| Color | Gray, opaque | Colorless, transparent | White, opaque | Colorless, transparent |
| Stretch to break (%) | 330 | 200-800 | 160 | 100 |
| Tensile strength (MPa) | 3.2 | 20-60 | 0.5-0.8 | 3.5 |
| Durometer (Shore A) | 35 | 20-60 | 35 & 65 | 45 |
| Method | CLIP | Drop-on-Demand | Polyjet | DLP |
| Proportion of silicone (%) | 30* | 100 | 70* | 65 |

*estimated

Sources:
Carbon: https://www.carbon3d.com/materials/silicone/
Wacker AG: https://www.aceo3d.com/silicones/
Keyence: https://eb-tec.de/wp-content/uploads/2017/09/Elastisches-Silikon-Druckmaterial.pdf One important aspect that distinguishes the invention from other 3D-printable silicones is that they have similar or better characteristics and, at the same time, can be printed using the established DLP method.

One preferred formulation contains 50 to 60% by weight of component a), because this enables correspondingly desired elastic materials to be produced. Threshold ranges in which a sufficient elastic material quality is just still produced are from 25 to 75%, preferably 35 to 65%.

For component b), the specified range of 20 to 50% by weight covers all ranges that are elastic or could otherwise be of interest. 20% by weight must be included in order to keep the viscosity of the overall composition low. More than 50% results in plastic objects and no longer elastic objects.

With regard to the component, it should be noted that the addition of this component is not mandatory. But it can improve the mechanical properties. Disadvantages can arise, however, because the objects may no longer be transparent or the viscosities may not be low enough.

With regard to component c), it should be noted that the use of silicone oil is essential. It lowers the viscosity and also increases the elastic properties in the system. Addition in the range from 1 to 25% by weight is variable and does not result in discoloration of the system.

With respect to component d), it should be noted that such fillers can also enhance the elastic behavior. They can lead to a thixotropy in excessive amounts, however, which negatively affects the flowability. A range of fillers from 0.5 to 10% by weight is preferred.

With regard to component e), it should be noted that a photoinitiator or a combination of photoinitiators is indispensable for the photocuring system. However, the concentrations can be reduced to 0.1 to 3% by weight without disadvantageously affecting the outcome.

With regard to the formulation, it should be noted that the inhibitors need not be added to the system separately; instead, they are contained in the monomers. A proportion by weight of no more than 0.5% by weight should be set.

With regard to the component, it should be noted that colorants are not desirable for the primary application but could nevertheless be used.

With regard to the component, it should be noted that it is not absolutely necessary to add UV stabilizers or flow additives in the final formulation. But they can be used.

The invention claimed is:

1. A transparent, elastic, and biocompatible 1K silicone material for additive manufacturing that can be printed by stereolithographic processes, the material comprising at least the following components:
   a) 25-75% by weight of a monomeric or oligomeric dimethacrylate based on silicone or silicone urethanes having a viscosity of <100 Pa·s,
   b) 20-50% by weight of one or more monomeric/oligomeric cyclic (meth)acrylates having a viscosity of <0.5 Pa·s,
   c) 1-25% by weight of silicone oil having a viscosity of <1 Pa·s,
   d) 0.5-20% by weight of fillers with a particle size of <100 μm,
   e) 0.1-5% by weight of one or a combination of a plurality of photoinitiators whose absorption is in the wavelength range of the laser beam or irradiation source used, and
   2-20% by weight of an aliphatic or cycloaliphatic dimethacrylate having a viscosity of <10 Pa·s.

2. The material according to claim 1, wherein component a) is included at 35 to 65% by weight.

3. The material according to claim 1, further comprising: 0.5 to 10% by weight of component d).

4. The material according to claim 1, wherein component e) is included at 0.1 to 3% by weight.

5. The material according to claim 1, further comprising: up to 0.5% by weight of one or more anaerobic inhibitors.

6. The material according to claim 1, further comprising: up to 5% by weight of colorants.

7. The material according to claim 1, further comprising: up to 5% by weight of UV stabilizers, adhesion promoters, and/or flow additives.

8. A transparent, elastic, and biocompatible 1K silicone material for additive manufacturing that can be printed by stereolithographic processes, the material comprising at least the following components:
   a) 25-75% by weight of a monomeric or oligomeric dimethacrylate based on n-functionalized silicone or n-functionalized silicone urethanes with a degree of siloxane of n=1-1000, a degree of urethane of m=0-20, and a viscosity of <100 Pa·s,
   b) 20-50% by weight of one or more monomeric/oligomeric cyclic methacrylates having a functionality of n<2 and a viscosity of <0.1 Pa·s and a molecular weight of <250,
   c) 2-20% by weight of an aliphatic or cycloaliphatic dimethacrylate having a viscosity of <10 Pa·s,
   d) 2-25% by weight of silicone oil having a viscosity of <1 Pa·s,
   e) 2-20% by weight of fillers with a particle size of <100 μm, f) 0.5-5% by weight of one or a combination of a plurality of photoinitiators whose absorption is in the wavelength range of the laser beam or irradiation source used.

9. The material according to claim 8, further comprising: up to 0.5% by weight of one or more anaerobic inhibitors in association with aerobic inhibitors known in stereolithography.

* * * * *